(12) United States Patent
Bates et al.

(10) Patent No.: US 9,358,338 B2
(45) Date of Patent: Jun. 7, 2016

(54) PARTICLE CASSETTES AND PROCESSES THEREFOR

(71) Applicant: Powder Pharmaceuticals Incorporated, Shatin (HK)

(72) Inventors: Nigel R. Bates, Oxford (GB); Philip T. Price, Oxford (GB)

(73) Assignee: Powder Pharmaceuticals Incorporated, Hong Kong (HK)

( * ) Notice: Subject to any disclaimer, the term of this patent is extended or adjusted under 35 U.S.C. 154(b) by 0 days.

(21) Appl. No.: 14/698,598

(22) Filed: Apr. 28, 2015

(65) Prior Publication Data

US 2015/0231332 A1    Aug. 20, 2015

Related U.S. Application Data

(63) Continuation of application No. 13/973,649, filed on Aug. 22, 2013, now Pat. No. 9,044,546, which is a continuation of application No. 12/612,586, filed on Nov. 4, 2009, now Pat. No. 8,540,665, which is a continuation of application No. PCT/GB2008/001483, filed on Apr. 25, 2008.

(30) Foreign Application Priority Data

May 4, 2007 (GB) .................................. 0708758.8

(51) Int. Cl.
*A61M 5/30* (2006.01)
*A61M 5/20* (2006.01)
(Continued)

(52) U.S. Cl.
CPC .............. *A61M 5/204* (2013.01); *A61M 5/2053* (2013.01); *A61M 5/2459* (2013.01); *A61M 5/3015* (2013.01); *A61M 5/31* (2013.01); *A61M 2005/3128* (2013.01); *A61M 2207/00* (2013.01); *A61M 2207/10* (2013.01);
(Continued)

(58) Field of Classification Search
CPC ............ A61M 5/2459; A61M 5/3015; A61M 15/0045; A61M 15/0048; A61M 15/0051
USPC ............................ 128/203.15; 604/68, 71, 72
See application file for complete search history.

(56) References Cited

U.S. PATENT DOCUMENTS

| 2,307,986 A | 1/1943 | Brown et al. |
| 3,674,028 A | 7/1972 | Ogle |

(Continued)

FOREIGN PATENT DOCUMENTS

| CN | 1284383 | 2/2001 |
| DE | 3204582 | 8/1983 |

(Continued)

OTHER PUBLICATIONS

Yu et al., "Particle Acceleration for Delivery Deoxyribonucleic Acid Vaccine into Skin In Vivo", *Review of Scientific Instruments*, vol. 72, No. 8, pp. 3390-3395, American Institute of Physics, Aug. 2001.

*Primary Examiner* — Gerald Landry, II
(74) *Attorney, Agent, or Firm* — Levine Bagade Han LLP

(57) ABSTRACT

An article for use in manufacturing particle cassettes comprising one or more single pieces of membrane having a plurality of gas flow passages bonded thereto. The article allows convenient manufacture of particle cassettes. Two such articles may be employed to provide a finished particle cassette and a production line in which a plurality of gas flow passages are conveyed on a single membrane is disclosed.

18 Claims, 8 Drawing Sheets

(51) Int. Cl.
*A61M 5/24* (2006.01)
*A61M 5/31* (2006.01)

(52) U.S. Cl.
CPC ... *Y10T 29/49826* (2015.01); *Y10T 428/24149* (2015.01); *Y10T 428/24157* (2015.01)

(56) References Cited

U.S. PATENT DOCUMENTS

| | | | |
|---|---|---|---|
| 3,686,822 A * | 8/1972 | Wolfelsperger | B65B 47/02 53/427 |
| 4,133,163 A | 1/1979 | Wilson | |
| 4,478,368 A | 10/1984 | Yie | |
| 4,555,872 A | 12/1985 | Yie | |
| 4,586,854 A | 5/1986 | Newman et al. | |
| 4,587,772 A | 5/1986 | Griffiths | |
| 4,615,649 A | 10/1986 | Sharpless | |
| 4,624,080 A | 11/1986 | Jakobsson | |
| 4,631,871 A | 12/1986 | Saunders | |
| 4,648,215 A | 3/1987 | Hashish et al. | |
| 4,663,893 A | 5/1987 | Savanick et al. | |
| 4,666,083 A | 5/1987 | Yie | |
| 4,668,190 A | 5/1987 | Overmyer | |
| 4,674,491 A | 6/1987 | Brugger et al. | |
| 4,708,214 A | 11/1987 | Krawza et al. | |
| 4,711,056 A | 12/1987 | Herrington et al. | |
| 4,715,535 A | 12/1987 | Mulder | |
| D299,536 S | 1/1989 | Robbins | |
| 4,807,814 A | 2/1989 | Douche et al. | |
| 4,809,706 A | 3/1989 | Watson et al. | |
| 4,817,874 A | 4/1989 | Jarzebowicz | |
| 4,829,724 A | 5/1989 | Miller et al. | |
| 4,913,699 A | 4/1990 | Parsons | |
| 4,934,111 A | 6/1990 | Hashish et al. | |
| 4,941,298 A | 7/1990 | Fernwood et al. | |
| 4,945,688 A | 8/1990 | Yie | |
| 4,951,429 A | 8/1990 | Hashish et al. | |
| 5,024,656 A | 6/1991 | Gasaway et al. | |
| 5,037,247 A | 8/1991 | Kaiser et al. | |
| 5,054,249 A | 10/1991 | Rankin | |
| 5,100,792 A | 3/1992 | Sanford et al. | |
| 5,155,946 A | 10/1992 | Domann | |
| 5,283,985 A | 2/1994 | Browning | |
| 5,301,878 A | 4/1994 | Sinclair et al. | |
| 5,312,335 A | 5/1994 | McKinnon et al. | |
| 5,312,577 A | 5/1994 | Peterson et al. | |
| 5,325,638 A | 7/1994 | Lynn | |
| D349,958 S | 8/1994 | Hollis et al. | |
| 5,335,459 A | 8/1994 | Dale | |
| 5,365,762 A | 11/1994 | Thompson | |
| 5,366,560 A | 11/1994 | Rubey et al. | |
| 5,383,851 A | 1/1995 | McKinnon et al. | |
| 5,473,947 A | 12/1995 | Buquet | |
| 5,503,627 A | 4/1996 | McKinnon et al. | |
| 5,505,566 A | 4/1996 | Gruber | |
| 5,514,026 A | 5/1996 | Schaffer | |
| 5,533,501 A | 7/1996 | Denyer | |
| 5,551,909 A | 9/1996 | Bailey | |
| 5,571,323 A | 11/1996 | Duffy et al. | |
| 5,584,807 A | 12/1996 | McCabe | |
| 5,588,901 A | 12/1996 | Rubey et al. | |
| 5,615,980 A | 4/1997 | Mauchle | |
| 5,616,067 A | 4/1997 | Goenka | |
| 5,630,796 A | 5/1997 | Bellhouse et al. | |
| 5,643,058 A | 7/1997 | Erichsen et al. | |
| 5,645,380 A | 7/1997 | Rutz | |
| 5,718,581 A | 2/1998 | Fernwood et al. | |
| 5,749,684 A | 5/1998 | Horn Feja | |
| D399,951 S | 10/1998 | Drach | |
| 5,860,598 A | 1/1999 | Cruz | |
| 5,865,796 A | 2/1999 | McCabe | |
| 5,873,680 A | 2/1999 | Huber et al. | |
| 5,876,267 A | 3/1999 | Kanda | |
| 5,893,397 A | 4/1999 | Peterson et al. | |
| 5,899,880 A | 5/1999 | Bellhouse et al. | |
| 5,906,858 A | 5/1999 | Huber et al. | |
| 5,951,531 A | 9/1999 | Ferdman et al. | |
| 5,954,232 A | 9/1999 | Shervington et al. | |
| 5,984,677 A | 11/1999 | Fernwood et al. | |
| 5,992,772 A | 11/1999 | Hibner et al. | |
| 6,004,286 A | 12/1999 | Bellhouse et al. | |
| 6,010,478 A | 1/2000 | Bellhouse et al. | |
| 6,012,653 A | 1/2000 | Gunther et al. | |
| 6,013,050 A | 1/2000 | Bellhouse et al. | |
| 6,040,004 A | 3/2000 | Matsumoto et al. | |
| 6,051,274 A | 4/2000 | Huber et al. | |
| 6,053,889 A | 4/2000 | Heinzen et al. | |
| 6,090,790 A | 7/2000 | Eriksson | |
| 6,093,021 A | 7/2000 | Rainey | |
| 6,123,068 A | 9/2000 | Lloyd et al. | |
| 6,132,395 A | 10/2000 | Landau et al. | |
| 6,168,587 B1 | 1/2001 | Bellhouse et al. | |
| 6,196,269 B1 | 3/2001 | Michael et al. | |
| 6,203,186 B1 | 3/2001 | Cruz | |
| 6,217,654 B1 | 4/2001 | Mauchle et al. | |
| 6,230,703 B1 | 5/2001 | Bono | |
| 6,280,302 B1 | 8/2001 | Hashish et al. | |
| 6,328,714 B1 | 12/2001 | Bellhouse et al. | |
| 6,475,181 B1 | 11/2002 | Potter et al. | |
| 6,592,545 B1 | 7/2003 | Bellhouse et al. | |
| 6,607,510 B2 | 8/2003 | Landau | |
| 6,613,360 B1 | 9/2003 | Maa | |
| 6,685,669 B2 | 2/2004 | Bellhouse et al. | |
| D488,862 S | 4/2004 | McCalmon et al. | |
| 6,737,101 B2 | 5/2004 | Maa | |
| 6,752,780 B2 | 6/2004 | Stout et al. | |
| 6,770,054 B1 | 8/2004 | Smolyarov et al. | |
| 6,802,826 B1 | 10/2004 | Smoliarov et al. | |
| 6,849,060 B1 | 2/2005 | Brooks et al. | |
| 6,881,200 B2 | 4/2005 | Bellhouse et al. | |
| 6,883,222 B2 | 4/2005 | Landau | |
| 6,893,664 B1 | 5/2005 | Burkoth et al. | |
| 6,987,228 B1 | 1/2006 | MacMichael et al. | |
| 7,029,457 B2 | 4/2006 | Rogatchev et al. | |
| 7,060,048 B1 | 6/2006 | Nat et al. | |
| 7,074,210 B2 | 7/2006 | Leon et al. | |
| 7,182,748 B1 | 2/2007 | Potter et al. | |
| 7,229,645 B2 | 6/2007 | Maa et al. | |
| 7,255,865 B2 | 8/2007 | Walker | |
| 7,358,451 B2 | 4/2008 | MacMichael et al. | |
| 7,479,281 B1 | 1/2009 | Walker | |
| 7,547,292 B2 | 6/2009 | Sheldrake et al. | |
| 7,547,293 B2 | 6/2009 | Williamson et al. | |
| 7,618,394 B2 | 11/2009 | Bellhouse et al. | |
| 7,868,260 B2 | 1/2011 | MacMichael et al. | |
| 7,909,793 B2 | 3/2011 | Kendall | |
| 7,942,846 B2 | 5/2011 | Bellhouse et al. | |
| 8,061,006 B2 | 11/2011 | Kendall et al. | |
| 2001/0003351 A1 | 6/2001 | Chen et al. | |
| 2001/0004681 A1 | 6/2001 | Landau | |
| 2001/0036801 A1 | 11/2001 | Taylor | |
| 2002/0000477 A1 | 1/2002 | Hara | |
| 2002/0087117 A1 | 7/2002 | Stout et al. | |
| 2002/0091353 A1 | 7/2002 | Bellhouse et al. | |
| 2002/0092521 A1 | 7/2002 | Sullivan et al. | |
| 2002/0092523 A1 | 7/2002 | Connelly et al. | |
| 2002/0123717 A1 | 9/2002 | Landau | |
| 2002/0123718 A1 | 9/2002 | Landau | |
| 2002/0188249 A1 | 12/2002 | Landau | |
| 2002/0188250 A1 | 12/2002 | Landau et al. | |
| 2002/0188251 A1 | 12/2002 | Staylor et al. | |
| 2003/0019558 A1 | 1/2003 | Smith et al. | |
| 2003/0065286 A1 | 4/2003 | Landau | |
| 2003/0088214 A1 | 5/2003 | Leon et al. | |
| 2003/0093030 A1 | 5/2003 | Landau | |
| 2003/0133833 A1 | 7/2003 | Thomas et al. | |
| 2003/0163111 A1 | 8/2003 | Daellenbach | |
| 2003/0225368 A1 | 12/2003 | Landau et al. | |
| 2004/0074076 A1 | 4/2004 | Landau | |
| 2004/0093835 A1 * | 5/2004 | Siegel | B65B 5/103 53/452 |
| 2004/0111054 A1 | 6/2004 | Landau et al. | |
| 2004/0111055 A1 | 6/2004 | Daellenbach | |
| 2004/0123864 A1 | 7/2004 | Hickey et al. | |

(56) References Cited

U.S. PATENT DOCUMENTS

| | | |
|---|---|---|
| 2004/0158197 A1 | 8/2004 | Bellhouse et al. |
| 2004/0159364 A1 | 8/2004 | Landau et al. |
| 2004/0195373 A1* | 10/2004 | Patel ................ A61M 15/0045 239/331 |
| 2004/0199106 A1 | 10/2004 | Landau et al. |
| 2004/0215135 A1 | 10/2004 | Sheldrake et al. |
| 2004/0255447 A1* | 12/2004 | Kendall ............... A61M 5/3015 29/428 |
| 2005/0010168 A1 | 1/2005 | Kendall |
| 2005/0027239 A1 | 2/2005 | Stout et al. |
| 2005/0075601 A1 | 4/2005 | Landau et al. |
| 2005/0101008 A1 | 5/2005 | Diresta et al. |
| 2005/0109659 A1* | 5/2005 | Hickey ............... A61M 15/0045 206/538 |
| 2005/0119608 A1 | 6/2005 | Landau et al. |
| 2005/0191361 A1 | 9/2005 | O'Connor et al. |
| 2005/0209553 A1 | 9/2005 | Landau |
| 2005/0209554 A1 | 9/2005 | Landau |
| 2005/0214227 A1 | 9/2005 | Prestrelski et al. |
| 2005/0230292 A1 | 10/2005 | Beden et al. |
| 2005/0271733 A1 | 12/2005 | Burkoth et al. |
| 2006/0089593 A1 | 4/2006 | Landau et al. |
| 2006/0089594 A1 | 4/2006 | Landau |
| 2006/0171953 A1 | 8/2006 | Cabezon Silva et al. |
| 2007/0235029 A1* | 10/2007 | Zhu ................... A61M 15/0045 128/203.12 |
| 2007/0277820 A1* | 12/2007 | Crowder ........... A61M 15/0045 128/203.12 |
| 2008/0041368 A1* | 2/2008 | Jones ................ A61M 15/0045 128/200.23 |
| 2008/0047866 A1* | 2/2008 | Quoniam .......... A61M 15/0045 206/531 |
| 2008/0071211 A1 | 3/2008 | Williamson et al. |
| 2008/0086079 A1 | 4/2008 | Williamson et al. |
| 2008/0161755 A1 | 7/2008 | Landau |
| 2008/0171968 A1 | 7/2008 | Stout et al. |
| 2008/0262417 A1 | 10/2008 | Kendall et al. |
| 2008/0300535 A1 | 12/2008 | Kendall et al. |
| 2009/0035623 A1 | 2/2009 | Tsuji |
| 2009/0137948 A1 | 5/2009 | Marshall et al. |
| 2009/0137949 A1 | 5/2009 | Landau et al. |
| 2009/0156992 A1 | 6/2009 | Landau |
| 2010/0112277 A1 | 5/2010 | Joseph et al. |
| 2010/0121262 A1 | 5/2010 | Bates et al. |
| 2010/0168710 A1* | 7/2010 | Braithwaite ...... A61M 15/0028 604/403 |
| 2010/0173005 A1 | 7/2010 | Prestrelski et al. |
| 2010/0298767 A1 | 11/2010 | Bates et al. |
| 2013/0338579 A1 | 12/2013 | Bates et al. |

FOREIGN PATENT DOCUMENTS

| | | |
|---|---|---|
| DE | 3326602 | 3/1984 |
| DE | 3516103 | 11/1986 |
| DE | 3531927 | 3/1987 |
| DE | 3612473 | 10/1987 |
| DE | 3634700 | 4/1988 |
| DE | 3727441 | 3/1989 |
| DE | 3805531 | 8/1989 |
| DE | 4040227 | 6/1992 |
| DE | 4209353 | 9/1993 |
| DE | 19937454 | 12/1993 |
| DE | 4313704 | 11/1994 |
| DE | 4322111 | 1/1995 |
| DE | 4329931 | 3/1995 |
| DE | 29603662 | 8/1996 |
| DE | 19541310 | 5/1997 |
| DE | 19600450 | 7/1997 |
| DE | 19729549 | 1/1999 |
| DE | 29905035 | 7/1999 |
| DE | 19804233 | 8/1999 |
| DE | 19807917 | 8/1999 |
| DE | 19838276 | 2/2000 |
| DE | 20010854 | 10/2000 |
| DE | 29923669 | 5/2001 |
| DE | 19961202 | 7/2001 |
| DE | 20106816 | 8/2001 |
| DE | 10017556 | 10/2001 |
| EP | 0119338 | 9/1984 |
| EP | 0197625 | 10/1986 |
| EP | 0295917 | 12/1988 |
| EP | 0427457 | 5/1991 |
| EP | 0445104 | 9/1991 |
| EP | 0458685 | 11/1991 |
| EP | 0469814 | 2/1992 |
| EP | 0471323 | 2/1992 |
| EP | 0515449 | 12/1992 |
| EP | 0518561 | 12/1992 |
| EP | 0525720 | 2/1993 |
| EP | 0621078 | 10/1994 |
| EP | 0629451 | 12/1994 |
| EP | 0651663 | 5/1995 |
| EP | 0725720 | 11/1995 |
| EP | 0711609 | 5/1996 |
| EP | 0782866 | 7/1997 |
| EP | 0783879 | 7/1997 |
| EP | 0880997 | 12/1998 |
| EP | 1011763 | 6/2000 |
| EP | 1038674 | 9/2000 |
| EP | 1202762 | 5/2002 |
| EP | 1229950 | 8/2002 |
| EP | 1267962 | 1/2003 |
| EP | 1365823 | 12/2003 |
| EP | 1443985 | 8/2004 |
| EP | 1485151 | 12/2004 |
| EP | 1551476 | 7/2005 |
| EP | 1636090 | 3/2006 |
| EP | 1745814 | 1/2007 |
| EP | 1748811 | 2/2007 |
| EP | 1866012 | 12/2007 |
| EP | 1979022 | 10/2008 |
| EP | 2068978 | 6/2009 |
| EP | 2076301 | 7/2009 |
| EP | 2092947 | 8/2009 |
| FR | 2534983 | 4/1984 |
| FR | 2565877 | 12/1985 |
| FR | 2580191 | 10/1986 |
| FR | 2602447 | 2/1988 |
| FR | 2604093 | 3/1988 |
| FR | 2645062 | 10/1990 |
| FR | 2666753 | 3/1992 |
| FR | 2759121 | 8/1998 |
| GB | 2189843 | 11/1987 |
| WO | WO 92/19384 | 11/1992 |
| WO | WO 93/23225 | 11/1993 |
| WO | WO 94/02188 | 2/1994 |
| WO | WO 94/24263 | 10/1994 |
| WO | WO 95/19799 | 7/1995 |
| WO | WO 95/24176 | 9/1995 |
| WO | WO 96/04947 | 2/1996 |
| WO | WO 96/12513 | 5/1996 |
| WO | WO 96/20022 | 7/1996 |
| WO | WO 97/34652 | 9/1997 |
| WO | WO 97/40963 | 11/1997 |
| WO | WO 97/47730 | 12/1997 |
| WO | WO 97/49525 | 12/1997 |
| WO | WO 98/22639 | 5/1998 |
| WO | WO 98/48873 | 11/1998 |
| WO | WO 98/52632 | 11/1998 |
| WO | WO 98/57691 | 12/1998 |
| WO | WO 99/49216 | 9/1999 |
| WO | WO 00/33899 | 6/2000 |
| WO | WO 00/48654 | 8/2000 |
| WO | WO 00/58147 | 10/2000 |
| WO | WO 01/13975 | 3/2001 |
| WO | WO 01/13977 | 3/2001 |
| WO | WO 01/33176 | 5/2001 |
| WO | WO 01/36159 | 5/2001 |
| WO | WO 01/74425 | 10/2001 |
| WO | WO 02/055139 | 7/2002 |
| WO | WO 02/070051 | 9/2002 |
| WO | WO 02/098479 | 12/2002 |
| WO | WO 03/011379 | 2/2003 |

(56) References Cited

FOREIGN PATENT DOCUMENTS

| WO | WO 03/011380 | 2/2003 |
|----|----|----|
| WO | WO 03/041762 | 5/2003 |
| WO | WO 03/072170 | 9/2003 |
| WO | WO 03/103752 | 12/2003 |
| WO | WO 2004/035107 | 4/2004 |
| WO | WO 2004/071558 | 8/2004 |
| WO | WO 2004/073554 | 9/2004 |
| WO | WO 2005/000680 | 1/2005 |
| WO | WO 2005/092000 | 10/2005 |
| WO | WO 2005/118033 | 12/2005 |
| WO | WO 2005/120607 | 12/2005 |
| WO | WO 2006/009839 | 1/2006 |
| WO | WO 2006/047087 | 5/2006 |
| WO | WO 2006/073394 | 7/2006 |
| WO | WO 2006/088513 | 8/2006 |
| WO | WO 2006/088630 | 8/2006 |
| WO | WO 2007/089727 | 8/2007 |
| WO | WO 2008/036291 | 3/2008 |
| WO | WO 2008/045161 | 4/2008 |
| WO | WO 2008/088609 | 7/2008 |
| WO | WO 2008/103997 | 8/2008 |
| WO | WO 2008/135719 | 11/2008 |
| WO | WO 2009/070603 | 6/2009 |
| WO | WO 2009/070605 | 6/2009 |

* cited by examiner

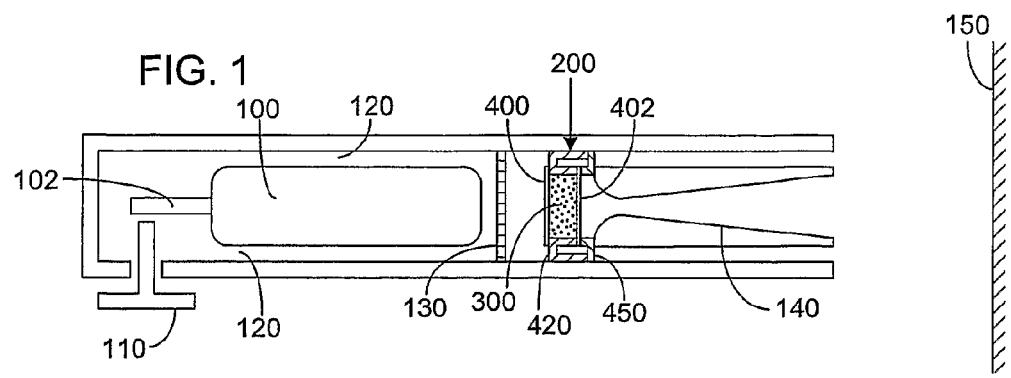
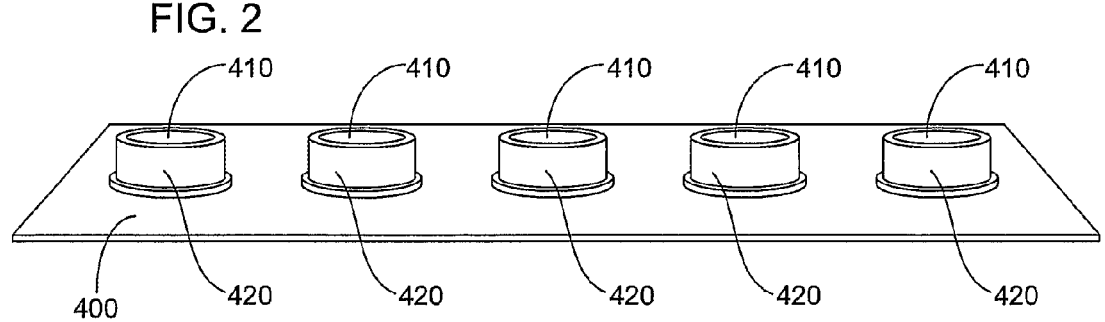
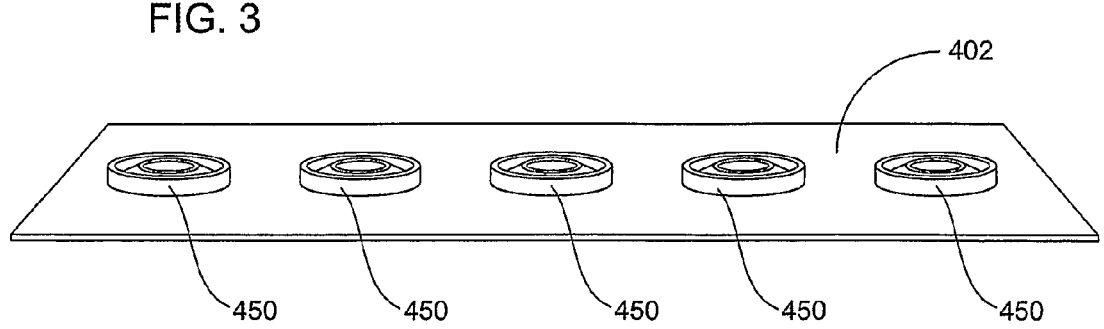

PARTICLE CASSETTES AND PROCESSES THEREFOR

CROSS-REFERENCE TO RELATED APPLICATIONS

This application is a continuation of U.S. patent application Ser. No. 13/973,649 filed Aug. 22, 2013, which is a continuation of U.S. patent application Ser. No. 12/612,586 filed Nov. 4, 2009, now U.S. Pat. No. 8,540,665, which is a continuation of PCT International Application No. PCT/GB2008/001483 filed Apr. 25, 2008, which claims priority to United Kingdom Patent Application No. 0708758.8 filed May 4, 2007, the contents of each of which are incorporated by reference herein in their entireties.

TECHNICAL FIELD OF THE INVENTION

The present invention relates generally to improvements in particle cassette technology. More specifically, the present invention relates to articles for use in manufacturing particle cassettes, said articles comprising a single piece of membrane film. The invention also relates to methods for providing such an article, methods of manufacturing particle cassettes, so-manufactured particle cassettes, devices for accelerating particles and methods of operating such devices.

BACKGROUND OF THE INVENTION

Needleless syringe devices are known from WO 94/24263. In this document, a needleless syringe is disclosed which entrains particles in a gas stream accelerated through a nozzle so that the particles may be injected into a target, such as human or animal skin or other cells. For many applications, there is a need for the particles to be maintained in a sealed and often sterile environment prior to actuation of the device. WO 94/24263 discloses a particle cassette comprising a central annular ring having rupturable membranes sealed to each face so as to form a self-contained sealed unit containing particles to be injected. Upon actuation of the device, the membranes rupture, allowing the particles initially contained between the membranes to be entrained in the gas flow and then delivered to the target. WO 94/24263 is hereby incorporated by reference.

An improvement to the particle cassette of WO 94/24263 is disclosed in WO 03/011379. In this document, a particle cassette comprised of two parts, each part having bonded thereto a rupturable membrane, is disclosed. In the preferred mode of manufacture, the membranes are heat-bonded to their respective cassette parts and the particle cassette is formed by bringing the cassette parts together so to create a chamber for the particles between the membranes. This overcomes the problem with the WO 94/24263 particle cassette that heat-bonding the second membrane to the annular ring can cause degradation of the particles in the chamber. WO 03/011379 is also hereby incorporated by reference.

The particle cassettes of WO 03/011379 comprise a minimum of four parts; a first cassette part, a first membrane bonded thereto, a second cassette part and a second membrane bonded thereto.

The initial step of bonding the first and second membranes to the respective first and second cassette parts is laborious. Initially, the first cassette part and first membrane have to be aligned with one another. Then, heat and pressure must be applied to bond the first membrane to the first cassette part. The same needs to be done for the second membrane and the second cassette part. Aligning the membranes with the respective cassette parts prior to bonding can be bothersome.

Another problem lies in accurately and quickly providing particles to the particle cassettes. One method for providing particles to a cassette part having a membrane bonded thereto is disclosed in WO 01/33176, the disclosure of which is hereby incorporated by reference. However, that method requires the cassette part (and attached membrane) to be placed on the weight measuring scale prior to particle dispensing and to be removed from the weight measuring scale after dispensation. This can be done manually although a mechanism for this purpose is shown in FIG. 20 of WO 01/33176. It should be appreciated that it is difficult in practice to implement such a mechanism with a high throughput of particle cassettes and which is reliable enough to grasp the particle cassette parts and carry them without spilling any particles. It can be especially difficult to orient the particle cassette parts properly on the weight measuring scales, especially if it is desired to bring the particle cassette parts to and from the scale at a high speed.

Furthermore, once the cassette parts have been bonded with their respective membrane, and one of the cassette parts has had particles provided to its chamber, it is necessary to relatively orient the first and second cassette parts before bringing them together to create a finished particle cassette.

Devices and methods which alleviate the laborious manufacturing process are thus desired.

BRIEF SUMMARY OF THE INVENTION

The invention addresses at least one of the above-mentioned problems by providing an article for use in manufacturing particle cassettes, said article comprising: a single piece of first membrane film capable of being ruptured by gas under pressure; and a plurality of gas flow passages; wherein each said gas flow passage is closed by said single piece of first membrane film.

The use of a single piece of first membrane film to close a plurality of gas flow passages helps to alleviate the problem of aligning the gas flow passages with the film prior to bonding. It is difficult to bind small circular pieces of membrane to the gas flow passage with high accuracy. If instead, the gas flow passage is bonded to a larger sheet of membrane the alignment of the passage on the membrane is not such an issue. A good bond between the membrane and the first cassette part (containing the gas flow passage) can be achieved wherever on the membrane film the gas flow passage is located. This contrasts with the prior art where it is necessary to exactly line-up the small circular membranes with the cassette parts. Any misalignment may result in the membrane not fully closing the gas flow passage.

The use of a single piece of first membrane film to close a plurality of gas flow passages also allows the film itself to be used in transporting the gas flow passages. This assists in the various orientation procedures that the cassette parts must go through in order to produce a finished particle cassette.

The use of a single piece of membrane film to close a plurality of gas flow passages also allows the step of bonding the first cassette part to the membrane film to be carried out for a plurality of particle cassette parts at the same time. In other words, a heat-bonding procedure can be carried out on a batch of first cassette parts (containing respective gas flow passages) that are attached to the same piece of membrane film.

The use of a single piece of membrane film to close a plurality of gas flow passages also provides an advantage in that the relative positioning of neighbouring gas flow passages can be fixed by the position of such passages on the film. Thus, in a production line environment, transporting the initial gas flow passage by a predetermined amount also serves to transport the other gas flow passages by the same amount (by virtue of each gas flow passage being attached to the same piece of membrane film). This assists in the various orientation and alignment processes that are needed to create a finished particle cassette.

The plurality of gas flow passages are preferably laterally offset from one another. Further, the plurality of gas flow passages are preferably all arranged on the same side of the single piece of first membrane film. In variations, however, the passages may be arranged on either one of the two sides of the first membrane film.

The gas flow passages may be closed by the film in a variety of arrangements. For example, the passages may be lined up on the film in a linear arrangement. Another arrangement is a two-dimensional grid of passages. Further, a circular arrangement is possible.

The gas flow passages may be provided inside a respective first cassette part, which first cassette part is dedicated to its own gas flow passage. Such first cassette parts are similar to those disclosed in WO 03/011379. As an alternative, a plurality of gas flow passages may be comprised in a single, unitary, first cassette part. This applies to all of the embodiments, including the linear embodiment, the two-dimensional embodiment, and the circular embodiment.

The membranes are attached to the cassette parts preferably by a heat-bonding process. The cassette parts are attached together preferably by a process that does not involve heat-bonding.

In one aspect, the present invention may be viewed as the use of a single piece of membrane film for a plurality of cassette parts.

It is possible for both of the membranes of the finished particle cassette to be part of a respective larger film that is shared with other particle cassettes. Alternatively, just one of the membranes may be part of a larger film shared with other cassettes, with the other membrane being dedicated to the particle cassette in question.

One or both of the particle cassette parts may be cut out of the film prior to assembly together. The advantages of improved orientation and alignment are still achieved even when the particle cassette parts are cut from the membrane prior to the final assembly.

The present invention further provides a method of making an article for use in manufacturing particle cassettes, said method comprising: attaching a single piece of first membrane film to a plurality of gas flow passages such that each gas flow passage is closed by said single piece of membrane film.

The method may involve a production line and the use of a single membrane film to carry a plurality of gas flow passages allows simplified means to be used for conveying the gas flow passages to desired locations, e.g. particle dispensing stations, sterilization stations and membrane cutting stations. For example, the single piece of membrane can be fed like a web, with the gas flow passages being carried on the "web". Another method is to use means to directly propel the initial gas flow passage, this being effective to also propel the other gas flow passages that follow by virtue of their mutual connection to the same membrane film.

For example, the use of a single piece of membrane film allows a plurality of gas flow passages to be accurately conveyed in rapid succession to a particle dispensing station in which particles are provided to the gas flow passage. Accurate and speedy conveying may then transfer the gas flow passages to an assembly station in which a second cassette part already having membrane film sealed thereto is attached to the first cassette to provide a particle cassette in which the particles are located between the two rupturable membranes.

Conveniently, this second cassette part is one of a plurality of cassette parts already attached to a single piece of second membrane film such that the second cassette part may be attached to the gas flow passage with the same ease of conveyance and orientation.

The use of a single piece of membrane film also allows the particle cassette, once assembled, to be rolled up and thereafter unrolled from a dispenser. This allows a magazine of particle cassettes to be provided in a cheap and convenient format and in which it is easy to index a cassette into a multi-use device.

The present invention also provides a device for accelerating a dose of particles, which device is designed to accept particle cassettes attached together by means of a single piece of membrane film.

Such a device typically comprises a gas supply conduit for supplying gas under pressure; a particle cassette exchange station downstream of said gas supply conduit; and a nozzle downstream of said particle cassette exchange station.

The device is typically constructed such that, in use, gas is supplied to said gas supply conduit and causes a loaded particle cassette to open, whereupon the gas entrains said dose of particles contained in said particle cassette and said gas and particles are accelerated by said nozzle.

In a preferred embodiment the particle cassette exchange station comprises a holder for holding in position a gas flow passage of said particle cassette, which gas flow passage is closed by said single piece of membrane film. The holder may be arranged to selectively release the held gas flow passage.

Additional gas flow passages are preferably closed by said single piece of membrane film. The device is preferably arranged to hold the gas flow passages as they line up with the gas supply conduit and nozzle. The holder is preferably arranged to hold the gas flow passage in position prior to and during activation of the device and the holder is preferably arranged to release the spent particle cassette after activation. The holder may thereafter hold another gas flow passage that is closed by the same piece of first (or second) membrane film.

A series of indexing holes may be provided down one or both sides of the membrane film, in the manner of movie film. In non-linear embodiments, such as circular embodiments, the indexing holes may be placed around the circumference of the film, and/or indexing may be achieved by a non-circular central hole.

BRIEF DESCRIPTION OF THE SEVERAL VIEWS OF THE DRAWINGS

Embodiments of the present invention will now be described, by way of example only, with reference to the accompanying schematic drawings, in which:

FIG. 1 shows a needleless syringe with a full particle cassette loaded in it;

FIG. 2 shows a single piece of membrane having attached to it a plurality of gas flow passages, which gas flow passages are comprised in separate first cassette parts;

FIG. 3 shows a single piece of membrane having attached to it a plurality of second cassette parts;

FIG. 4 is an exploded cross-sectional view of one of the first cassette parts of FIG. 2 as it is brought into contact with one of the second cassette parts of FIG. 3;

FIG. 5 shows the two single pieces of membrane of FIGS. 2 and 3 when attached together by the first and second cassette part, to provide a strip of particle cassettes;

DESCRIPTION OF PREFERRED EMBODIMENTS

Figure 4:
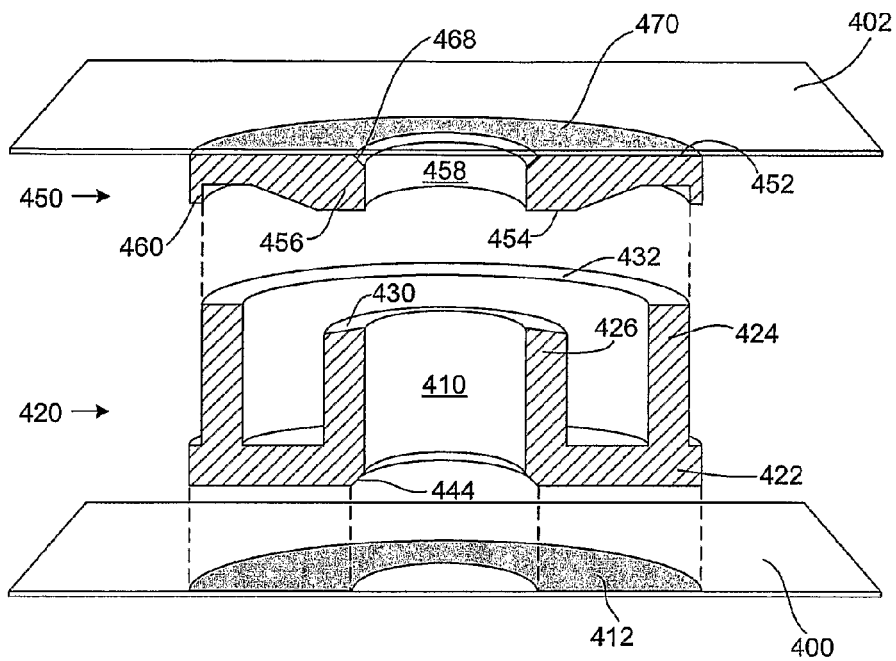

In the drawings, components are not necessarily drawn to scale. The drawings are schematic for reasons of clarity. In reality the thickness of the rupturable membrane film may be much less than is shown and/or the volume of particles may be so small as to be barely visible to the naked eye.

FIG. 1 shows a needleless syringe device which accepts and utilizes a particle cassette, which particle cassette can be an embodiment of the present invention. The needleless syringe comprises a reservoir 100 of compressed gas, typically helium at super-atmospheric pressure of, for example, 5-200 bar, preferably 15-80 bar, more preferably 20-60 bar. The reservoir 100 is in the form of a bulb having a frangible tip 102. An actuation button 110 is provided at one end of the device and is positioned such that depressing the button causes it to bear against the frangible tip 102 so as to break the frangible tip 102 of the reservoir 100. Gas at super-atmospheric pressure is thus released from the reservoir 100 and flows around the outside of reservoir 100 down passages 120, in the manner described in EP 0,914,754. The gas passes through a filter 130 before reaching the particle cassette generally designated as 200. The particle cassette comprises a first cassette part 420 having a first rupturable membrane 400 bonded thereto and a second cassette part 450 having a second rupturable membrane 402 bonded thereto. Particles 300 are located in the gas flow passage, which forms a chamber, between the membranes.

The pressure of the gas released from the reservoir 100 causes the membranes 400, 402 to successively burst such that the particles 300 are entrained in the gas stream. The gas stream (containing the particles) is thereafter accelerated in a nozzle 140, preferably of convergent-divergent configuration, towards a target 150. The target 150 is preferably human skin or other tissue of a living human or animal. The device is configured, and more particularly the gas pressure and membrane thickness are selected, to ensure a desired penetration of particles to the target. Different particles may be used for different purposes and may require different penetration depths to be effective. The exact gas pressure used is therefore a function of the particle type and the target type.

It will be appreciated that this description of the device is merely exemplary and modifications may be made in accordance with the teachings of the prior art concerning such needleless syringe devices. For example, the reservoir 100 may comprise a valve rather than a frangible tip and may be positioned such that the gas flows directly out and towards the filter 130 rather than having to turn 180° upon exiting the reservoir 100. A further alternative is to replace the reservoir 100 by two valves (as in FIG. 15), the downstream valve being connected to the actuation button and the upstream valve being connected to a larger source of pressurized gas. Prior to actuation, the upstream valve is opened to charge with gas a chamber in between the two valves and is thereafter closed. Upon pressing the actuation button, the downstream valve opens thereby releasing the charge of gas. This allows an effective multi-use device to be provided. The various means that may be used to provide the gas supply mean that the supply of gas is not an essential aspect of the invention.

Further, a silencing system and a spacer for spacing the nozzle exit from the target (neither shown in FIG. 1) may be provided as is known in the art.

The particle cassette of the present invention is generally applicable to any type of needleless syringe in which particles are picked up and entrained in a gas flow.

It will be appreciated that the downstream membrane 402 is, prior to actuation of the syringe, exposed to the atmosphere via the opening of the nozzle 140. To ensure that the particles are hermetically sealed from the atmosphere prior to use of the syringe, the present invention provides that no gases in the atmosphere can infiltrate between the cassette parts 420, 450 to the space where the particles 300 are located.

FIG. 2 shows an article for use in manufacturing particle cassettes according to the present invention.

The article comprises a single piece of first membrane film 400. In this embodiment the single piece of first membrane film is in the form of a strip having a longitudinal dimension much longer than its width and the longitudinal dimension and the width being much greater than the thickness (which is shown exaggerated in FIG. 2). Attached to the membrane are a plurality of gas flow passages 410. As shown in FIG. 2, the lower end of each gas flow passage 410 is completely closed by the first membrane film 400. Thus, any particles 300 which are placed inside the gas flow passages 410 of FIG. 2 would only be able to escape through the upper end of the gas flow passage 410. The passages in this embodiment are placed in a line on the same side of the membrane film. The passages are laterally offset from one another (that is to say, the passages do not line up longitudinally to provide a longer resultant gas flow passage).

In the embodiment of FIG. 2, each gas flow passage 410 is comprised in a separate first cassette part 420. This cassette part 420 is shown in more detail in FIG. 4. The membrane film is bonded, preferably heat-bonded, to each first cassette part 420 in a hermetic manner.

As can be seen from FIG. 4, the first cassette part 420 comprises a first annular protrusion 424 extending around the outermost periphery of the first cassette part 420. The purpose of this protrusion is to interact with corresponding features 460 of the second cassette part 450 so as to keep the two cassette parts together. The first annular protrusion 424 has at its uppermost end a ring-shaped face 432. A second annular protrusion 426 is provided radially inwardly of the first annular protrusion 424. This annular protrusion 426 surrounds and defines the gas flow passage 410 mentioned above. Furthermore, in the assembled particle cassette, this gas flow passage 410 forms, or forms part of, the particle confinement chamber. The second annular protrusion 426 has at its end a ring-shaped sealing face 430. This sealing face 430 is designed to seal against a corresponding face 454 of the second cassette part 450 as shown in FIG. 4. It may also seal against the rupturable membrane itself, as shown in FIG. 7 (described later).

Figure 7:
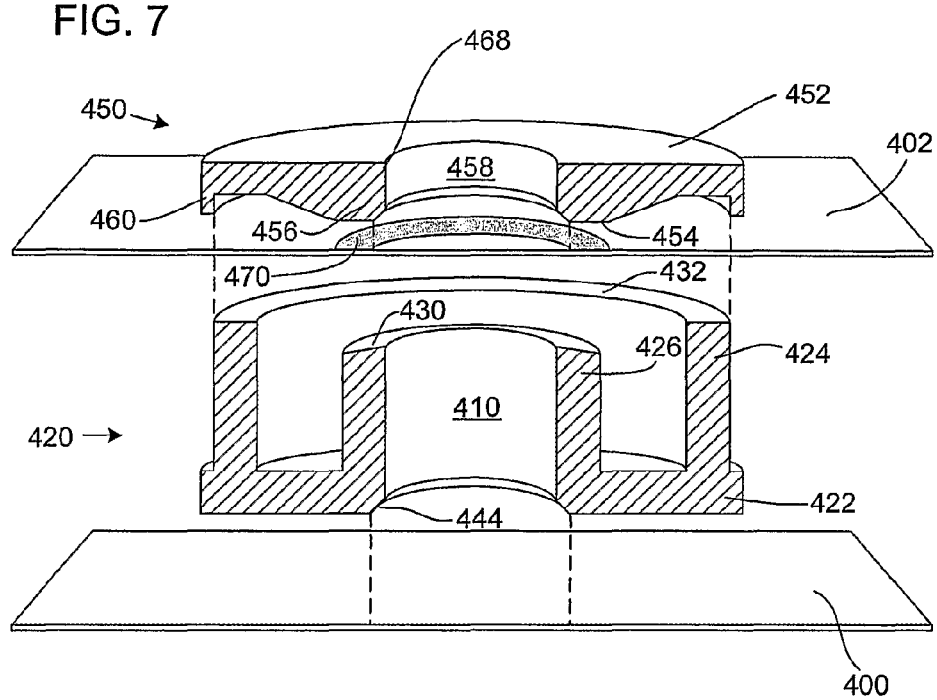
FIG. 7 shows an exploded cross-sectional view of the second cassette part of FIG. 6 when used with the first cassette part of FIG. 2.

As shown in FIGS. 4 and 7, the sealing face 430 is tapered such that the face is nearer to the top of the first cassette part at its radial innermost extent than it is at its radial outermost extent. This assists in providing a good seal and the taper may alternatively be provided in the other direction to achieve the same effect. The taper is preferably very shallow, for example 5° from the plane perpendicular to the longitudinal central axis of the first and second cassette part (i.e. the plane of the membrane 400 in FIG. 4). The taper is designed to be very shallow so that the sealed surface area increases relatively quickly as the two cassette parts are moved closer together to allow a larger seal area to be obtained with quite small longitudinal displacements of the cassette parts. Other values for the taper such as 10° and 15° may equally be used.

The first cassette part 420 preferably has a filleted edge 444 at the section that interacts with the first membrane 400. This fillet 444 provides an area where excess material can flow that is created during the heat-bonding procedure. This prevents material extending inwardly of the inner radius of the gas flow passage 410 and helps to ensure repeatable and desirable bursting characteristics for the membrane 400 during use.

The bottom face of the first cassette part 420 has a flange 422 which provides for an increased footprint 412 so as to maximize the bonding area between the first cassette part 420 and the membrane 400.

FIG. 3 shows a plurality of second cassette parts 450 attached to a single piece of second membrane film 402. The second cassette parts 450 are, similar to FIG. 2, arranged in a linear formation with equal spaces between each adjacent second cassette part 450. The spacing between the cassette parts is the same as the spacing between the first cassette parts 420 in FIG. 2.

As shown in FIGS. 4 and 7, the second cassette part 450 has a different design to the first cassette part 420. The second cassette part 450 comprises a base surface 452 to which the second membrane film 402 is bonded, preferably heat-bonded. As with the first cassette part and the first membrane film, such heat-bonding creates a hermetic seal between the second cassette part 450 and the second membrane film 402. The second cassette part 450 comprises an annular protrusion 456 which defines a passage 458 at its radially inward extent. In the configuration of FIG. 4, this passage 458 is also a gas flow passage and becomes an extension of the gas flow passage 410 in the assembled particle cassette. As such, the passage 458 also serves as part of the particle confinement chamber in the FIG. 4 embodiment. This annular protrusion 456 also defines a sealing face 454 that, in the assembled particle cassette, is aligned with the sealing face 430 of the first cassette part 420. As the first and second cassette parts are brought together, face 430 comes into contact with face 454 and the face 430 preferably undergoes plastic deformation so as to ensure a tight seal between the cassette parts.

The second cassette part 450 preferably comprises an outer annular protrusion 460 which in the assembled cassette, interacts with the first annular protrusion 424 of the first cassette part 420 so as to allow the first and second cassette parts to be held together. An interference fit is preferably provided between the inside of annular protrusion 460 and the radially outermost wall of first annular protrusion 424. Of course, such an interference fit can be replaced with other types of fit known in the art, including screw fits, snap fits and bonded fits. It is, however, preferable that the first cassette part 420 is joined to the second cassette part 450 by a method that does not involve heat-bonding in order to ensure that any particles located in gas flow passage 410 are not degraded by a subsequent heat-bonding process.

The annular protrusion 460 and/or the annular protrusion 424 need not be continuous around the entire circumference of the second and first cassette parts respectively. Indeed, it may be beneficial to have breaks in one or both of these protrusions such that air may escape from the space inside the particle cassette as the two cassette parts are brought together. This helps to prevent "barrelling" of the membranes as air pressure is increased inside the particle cassette during assembly.

The second cassette part 450, like the first cassette part 420, has a fillet 468 at the edge of the inner circumference that interacts with the membrane film 402. Again, this provides space for materials to flow into during the heat-bonding procedure.

Figure 13:
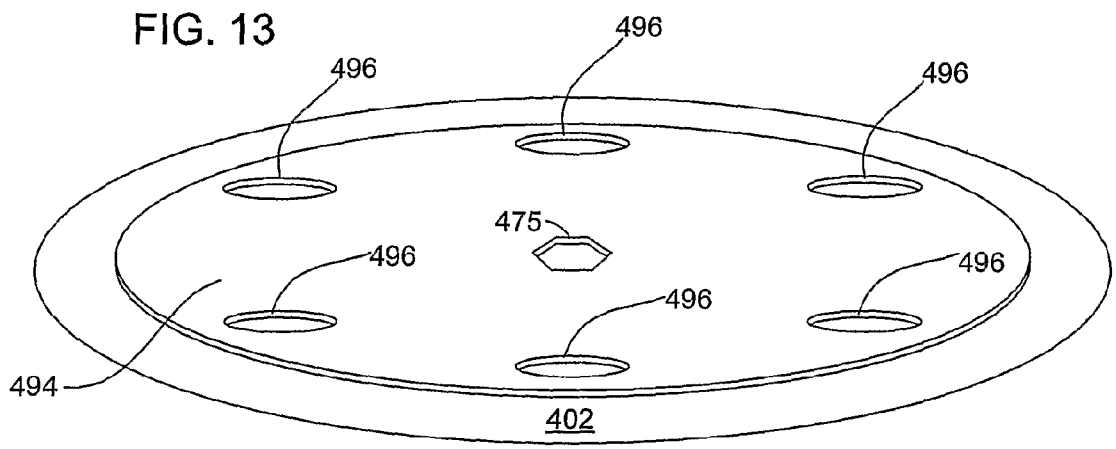
FIG. 13 shows a single, unitary, second cassette part designed to interact with the first cassette part of FIG. 12 to provide a plurality of particle cassettes.
Figure 14:
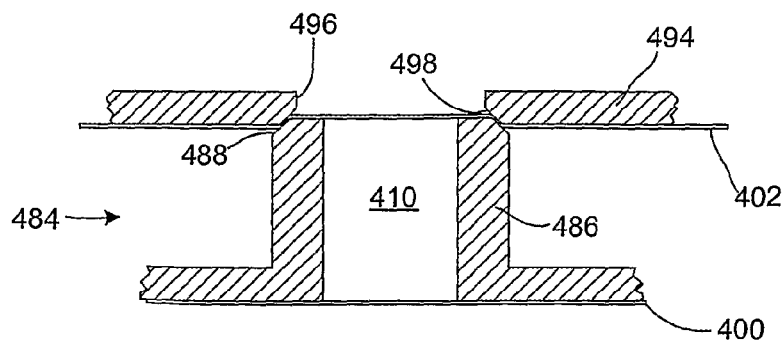
FIG. 14 is a close-up of the interaction between the first cassette part of FIG. 12 and the second cassette part of FIG. 13.

The particle cassette parts may be designed similar to FIGS. 13 and 14 of WO 03/01379. Any means for attaching the cassette parts together including interference fits, snap fits, screw fits etc. may be utilized. Furthermore, the design of FIGS. 4 and 7 may be adapted such that the first annular protrusion 424 on the first cassette part 420 araiularly engages outside of a corresponding inward annular protrusion provided on the second cassette part 450. In this case, the annular protrusion 460 on the second cassette part 450 is not required. This applies to all embodiments, including those where the second rupturable membrane film 402 is provided on the outside of, or on the inside of, the second cassette part 450.

Either or both of the rupturable membrane films 400, 402 may be provided by PET membranes, such as Mylar™. The preferred embodiment utilizes 15 μm thick PET membranes for both the first and second membrane films 400, 402. In general, any material that is capable of operating as a bursting membrane in a needleless syringe may be used, including polycarbonate or oriented polypropylene. Thickness ranges for the membranes include 5 μm to 50 μm, preferably 10 to 30 μm, more preferably 15 to 25 μm. Embodiments may use 19 μm or 20 μm thicknesses if desired.

Figure 5:
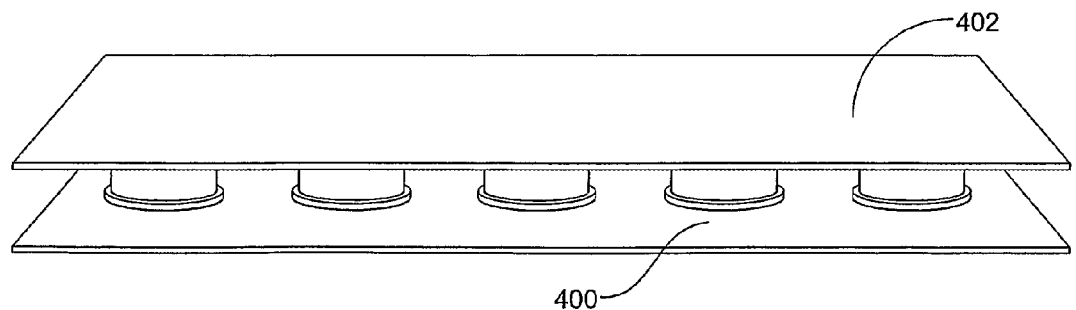

Once a plurality of first cassette parts have been attached to the first membrane 400, as shown in FIG. 2, and a plurality of second cassette parts 450 have been attached to the second membrane 402, as shown in FIG. 3, corresponding first and second cassette parts can be brought together, in the manner shown in FIG. 4 in order to achieve the structure shown in FIG. 5.

In FIG. 5, the first membrane 400 and second membrane 402 are arranged parallel to one another and spaced apart by a distance equivalent to the thickness of the particle cassette when assembled, hi between the two membranes, in the gas flow passage 410 and 458, lies a hermetic space for the confinement of particles.

Figure 6:
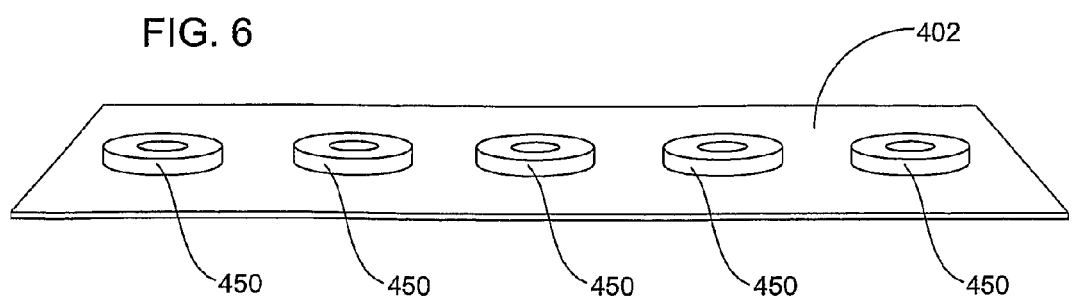
FIG. 6 shows an alternative arrangement of the second cassette part, whereby the single piece of membrane is bonded to the inner-face of the second cassette part.

FIG. 6 shows an alternative way of attaching the second cassette parts 450 to the second membrane 402. In particular, in the embodiment of FIG. 6, the second cassette parts 450 are attached to the membrane via the sealing face 454 rather than via the base surface 452. This attachment is shown in more detail in FIG. 7. It can be seen from bonding footprint 470 shown in FIG. 7 that the area of bond between the second particle cassette part 450 and the second membrane 402 is much smaller that the corresponding area 470 shown in FIG. 4. Nevertheless, this embodiment is thought to be advantageous because the second membrane 402 is "sandwiched" between the first and second cassette parts rather than being on the outer surface of the second cassette part 450.

In a needleless syringe device in which the gas flow direction is from the first cassette part to the second cassette part, i.e. the gas flow direction is upwards as shown in FIGS. 4 and 7, it is advantageous that the second cassette part 450 is encountered by the gas after the second membrane 402. The reason for this is that the impact of the gas on the second membrane 402 in the FIG. 4 arrangement could cause debonding of the membrane from the outer base surface 452 of the second cassette part 450. This would affect the rupturing characteristics of the membrane in an adverse manner. The provision of the second cassette part 450 on the downstream side of the second membrane 402 in the FIG. 7 arrangement helps to prevent this from occurring and helps to ensure proper rupturing of the membrane 402 upon activation in a needleless syringe device. The fact that the membrane 402 must follow a labyrinthine path around the annular protrusion 424 and around the annular protrusion 460 also helps to improve the interference fit between the protrusion 424 and protrusion 460.

Figure 8:
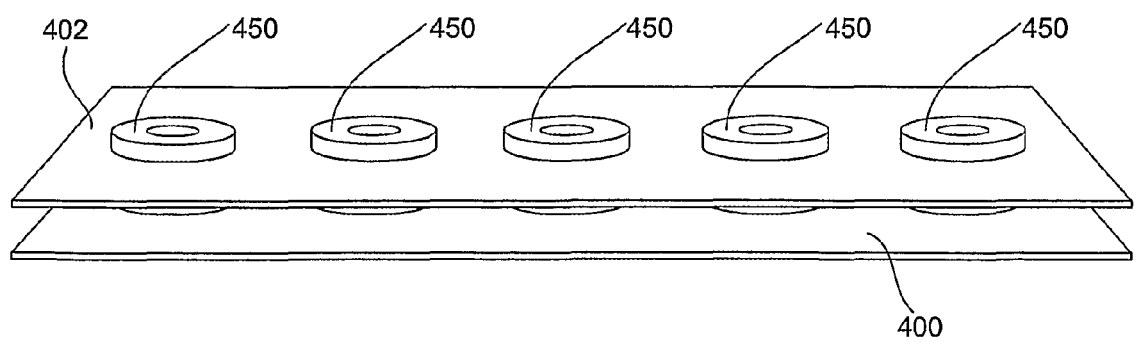
FIG. 8 shows an assembled strip of particle cassettes made according to FIG. 7.

FIG. 8 shows a strip of particle cassettes created by attaching the membrane 402 and second cassette part 450 of FIG. 6 to the membrane 400 and first cassette parts 420 of FIG. 2.

Figure 9:
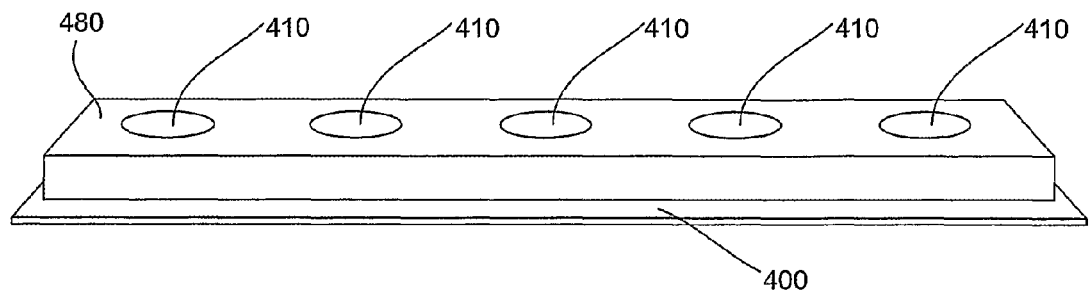
FIG. 9 shows a plurality of gas flow passages located in a single, unitary, first cassette part.
Figure 10:
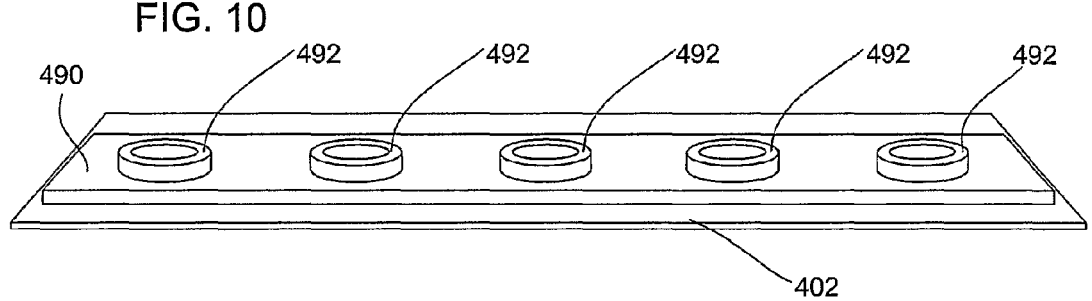
FIG. 10 shows a single, unitary, second cassette part attached to a single piece of membrane.

FIGS. 9 and 10 show an alternative embodiment of first and second cassette parts in which a plurality of gas flow passages 410 are provided in a single piece, unitary, first cassette part 480. This cassette part 480 is in turn bonded to the membrane 400. This allows for an increased area of bonding between the first cassette part 480 and the membrane 400. However, unless the first cassette part 480 is made from a quite flexible material, it does mean that the resulting strip of particle cassettes is less flexible than the FIG. 5 or FIG. 8 embodiments. The resulting strip can therefore only be rolled onto a roll of greater radius than the FIG. 5 or FIG. 8 embodiments.

FIG. 10 shows a single piece, unitary, second cassette part 490 having a series of annular protrusions 492 extending there from. These annular protrusions are designed to interact with, and insert into, the gas flow passage 410 of the first cassette part 480 shown in FIG. 9.

As in the FIG. 8 embodiment, it would be possible to bond the second membrane 402 to the other side of the second cassette part 490, i.e. to the outer ring-shaped faces of the annular protrusions 492 rather than to the flat base surface of the second cassette part 490. This would provide the advantages of "sandwiching" once the protrusions 492 (with the membrane 402 bonded thereto) are inserted into the gas flow passages 410 of the first cassette part 480 shown in FIG. 9.

The embodiments of FIGS. 2, 3, 5, 6, 8, 9 and 10 employ a linear configuration of first and second cassette parts on the membranes. The membranes are thus necessarily in the form of a strip having a very long longitudinal dimension, a comparatively short width dimension and a very small thickness dimension. Although five particle cassette parts are shown in the drawings, many more can be provided in practice. The linear orientation of the cassette parts offers the possibility of assembling the cassettes in an automated production line process. Conventional web handling and conveying apparatus may be used to move the gas flow passages from one station to another, as will be explained later. It is entirely within the scope of the present invention to have more than one line of particle cassette parts such that a two-dimensional grid of cassette parts is built up on the membrane.

Other embodiments, which utilize a circular layout of cassette parts, will be explained with the reference to FIGS. 11 to 14 of the accompanying schematic drawings.

Figure 11:
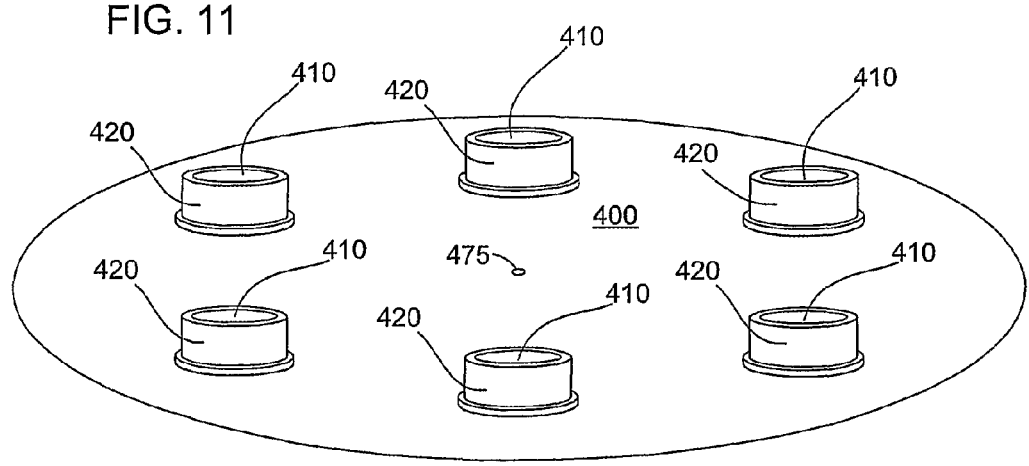
FIG. 11 shows a plurality of gas flow passages arranged in a circular formation on a single piece of membrane.

FIG. 11 shows a first piece of membrane film 400 having attached thereto a plurality of laterally offset first cassette parts 420 comprising gas flow passages 410. The first cassette parts 420 are of substantially the same design as the cassette parts shown in FIGS. 2, 4 and 7. The cassette parts are arranged in a substantially circular formation on the membrane 400, which membrane is shown itself to be circular but need only be of sufficient expanse to accommodate the cassette parts. Indeed, the membrane 400 could be ring shaped or could have more than one "circle" of particle cassettes disposed on it. As in the other embodiments, the gas flow passages are all on the same side of the film, although this is not essential.

Figure 12:
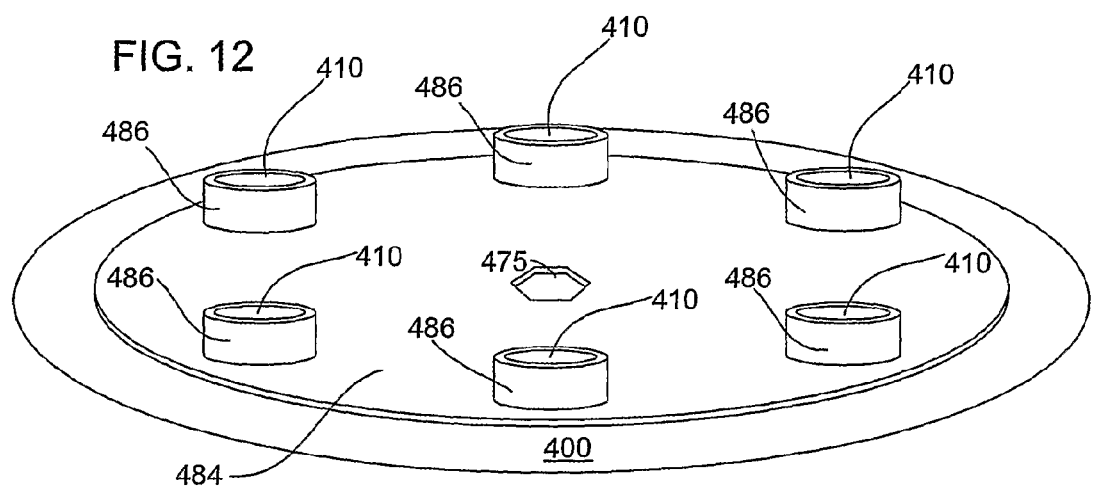
FIG. 12 shows a circular arrangement of a plurality of gas flow passages located in a single, unitary, first cassette part.

FIG. 12 shows an alternative embodiment to FIG. 11 in which each of the gas flow passages 410 are comprised in a single, unitary, first cassette part 484. The gas flow passages 410 are defined by annular protrusions 486 as shown in FIG. 12. Such a configuration has an advantage that the first cassette part 484 may be moulded as a single piece and the spacing of the various protrusions 486 can thus be set in the moulding process rather than being set in the heat-bonding process (as it would have to be with the embodiment of FIG. 11).

FIG. 13 shows a single piece unitary second cassette part 494 for use with either the FIG. 11 or FIG. 12 configuration. The second cassette part 494 is simply a flat sheet bonded to the membrane 402. The flat sheet second cassette part 494 has plurality of apertures 496 provided therein which are designed to line up with the protrusions 486 of the second cassette parts 484 shown in FIG. 12 or with the first cassette parts 420 shown in FIG. 11. FIG. 14 shows in more detail the attachment of the cassette parts and shows that the apertures 496 may be provided with a fillet 498 and shows that the upper surface of the protrusions 486 or the upper surface of the first cassette part 484 may be provided with a corresponding fillet 488. These fillets are designed to interact together to "sandwich" the second membrane 402 in the manner shown in FIG. 14, thereby creating a good seal for any particles located in the gas flow passage 410.

As an alternative, the second cassette part 494 can be inverted such that it interacts directly with the first cassette part 484 or 420. In this case, the membrane 402 would lie on the outer surface of the assembled particle cassettes rather than being "sandwiched" as shown in FIG. 14.

It is not necessary for the second cassette part 494 to be unitary. Indeed, the second cassette part 494 shown in FIG. 14 could be replaced by 6 annular ring sections individually bonded to the membrane 402 and which line up with the protrusions 486 of the first cassette part 484 or line up with each cassette part 420 shown in FIG. 11. Furthermore, the design of the second cassette part (i.e. the simplified aperture design) disclosed in FIG. 13 for the circular embodiment can equally be applied to the linear embodiment. Furthermore, the second cassette part design shown in FIGS. 3 and 6 can equally be applied to the circular embodiment.

FIG. 11 shows a small aperture 475 in the membrane 400. This aperture may be used by any particle acceleration device to locate the centre of rotation that enables successive particle cassettes to be brought into alignment with the gas flow passages of the particle acceleration device.

FIGS. 12 and 13 shows an embodiment in which this hole has a non-circular shape, such as a hexagonal shape. This aids in the indexing of the particle cassettes in any particle acceleration device.

Figure 15:
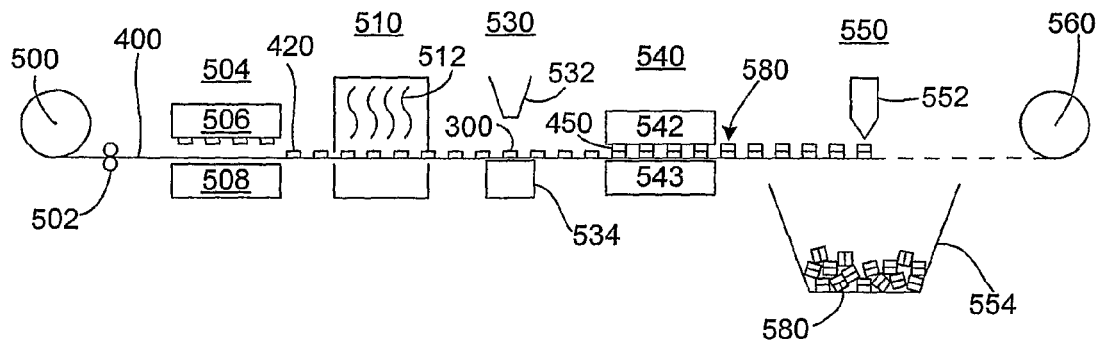
FIG. 15 is a diagram of a first embodiment of production line according to the present invention.

FIG. 15 shows an embodiment of a production line according to the present invention. This embodiment shows the manufacture of an article for use in manufacturing particle cassettes according to the present invention. It also shows how the first part of the particle cassette can be manufactured. Complete particle cassettes may also be made on this production line.

A long strip of first membrane film 400 is wound up on a roll 500. It may be fed from the roll 500 by means of rollers 502 or any other feeding means. The roll of membrane film 400 is firstly passed through a first cassette part attaching station 504.

In this embodiment, the first cassette part attaching station comprises two platens 506, 508 which can be brought together to attach a plurality of first cassette parts 420 to the membrane film 400. As shown in FIG. 15, four first cassette parts 420 are attached at one time. However, more or less cassette parts (including only a single cassette part 420) may be attached. The lower platen 508 may be heated so as to heat bond the membrane 400 to the cassette parts 420. Furthermore, although a plurality of separate cassette parts 420, each having a single gas flow passage 410, is shown in FIG. 15, the same method can be used to attach a unitary first cassette part 480, for example as shown in FIG. 9.

Once the first cassette part 420 has been attached to the membrane 400, the cassette part and membrane may be sterilized in a sterilization station 510. This station provides high energy particle radiation 512 (for example electron beam radiation or gamma radiation) to the first particle cassette parts 420 and the membrane 400 for a certain amount of time to sterilize the cassette parts and membrane. At this point, the production line may finish, the result being an article for use in the manufacture of particle cassettes, which article can be stored for several weeks or months prior to being used in a particle cassette. The article may be wound on a roll for storage. Stations 530, 540 and 550 in FIG. 15 are thus optional.

Alternatively to storing the articles, the first particle cassette parts may immediately have particles 300 dispensed into their gas flow passages 410. This can be achieved at the particle dispensing station 530, which may be similar to the particle dispensing apparatus disclosed in WO 01/33176. This apparatus comprises a hopper 532 containing the particles 300 to be dispensed and a dispensing nozzle at its lower end and a weight measuring scale 534. This is a gravimetric system of particle dispensing but other systems, such as volumetric dispensing, may be used. A certain weight, or volume, of particles is provided to the gas flow passage 410, adjacent to the membrane film 400.

Once the first particle cassette parts 420 have been provided with particles, a second cassette part 450 may be assembled to the first cassette part 420 so as to provide a complete particle cassette 580. This is achieved at the particle cassette assembling station 540 which attaches the first and second cassette parts together. In this embodiment, two platens 542, 543 are used to press the second cassette part 450 onto the first cassette part 420, with enough force to ensure an adequate seal. In this embodiment, the second particle cassette parts 450 are shown as separate entities, with each one being assembled to a corresponding first particle cassette part 420 separately. However, a plurality of second cassette parts, perhaps attached together by means of a second membrane film, may be connected to the first cassette part. This is shown in greater detail in FIG. 17.

Returning to FIG. 15, after the particle cassettes 580 have been assembled, they may be cut out from the membrane film 400 by means of a laser cutting station 550 which in this embodiment comprises a laser 552 and a hopper 554. The cut out particle cassettes 580 fall into the hopper 554 after cutting whereas the membrane film 400, having holes in where the particles cassettes were, is wound up on a reel 560.

Figure 16:
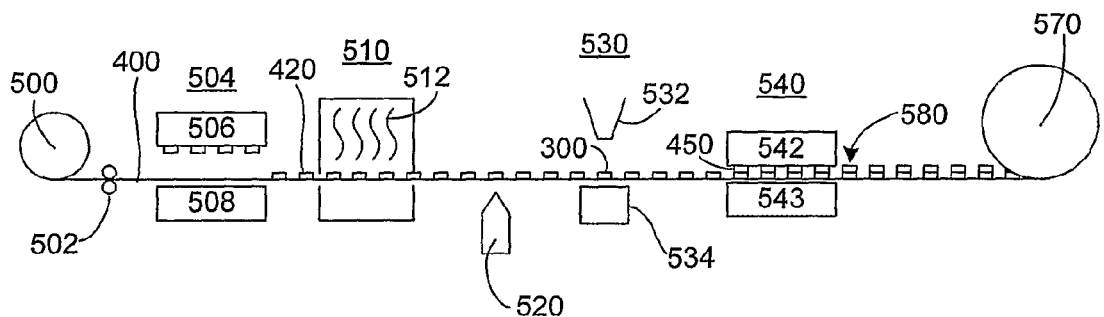
FIG. 16 is a diagram of a second embodiment of production line according to the present invention.

FIG. 16 shows an alternative embodiment in which an optional laser perforating station 520 is used to create perforations which do not fully cut out the first particle cassette parts 420 from the membrane 400. The finished particle cassettes are wound up onto the reel 570 without being removed from the membrane 400 but may easily be later detached from the membrane 400 by virtue of the perforations. The perforating stage 520 may be located at any point prior to the reel 570 and after the cassette part attaching stage 504. The perforating stage 520 may be replaced by a cutting stage 550 similar to that described above. Thus, one or both cassette parts may be cut from the film before or after being attached together, and before or after dispensing particles.

Figure 17:
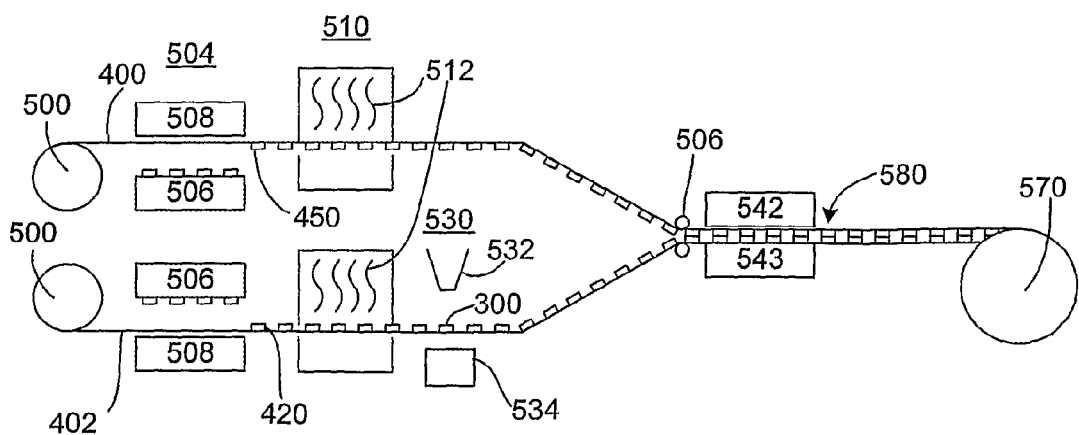
FIG. 17 shows a production line according to a third embodiment of the invention.

FIG. 17 shows an embodiment in which both of the cassette parts are attached to a respective single membrane film, and remain attached even after assembly of the particle cassettes 580. The assembled particle cassettes 580 are wound up on a reel 570 to create a magazine of particle cassettes. Rollers 506 are used to feed and orient the membranes 400, 402. Any standard feeding and/or conveying means may be used, including means that interact directly with the cassette parts 420, 450 instead of the membranes 400, 402. Instead of being wound on roll 520, the cassette parts may be cut out using a cutting station 550, similar to that shown in FIG. 15.

The advantage of these production lines is that the position of the first or second particle cassette parts may be defined with reference to the position of the membrane 400, 402.

As such, it is easier to align the particle cassette parts in the various stations and in particular in the particle dispensing station 530 and the particle cassette assembling station 540. Furthermore, keeping the particle cassette parts attached to the membrane 400 and/or 402 allows a magazine of particle cassettes to be easily provided with no additional parts.

FIGS. 15 to 17 show examples of production lines in which the cassette parts 420, 450 are the separate cassette parts shown in FIGS. 2 to 8. However, the production line is equally applicable to the unitary cassette parts shown in FIGS. 9 and 10. If the cassette parts 480, 490 are made from nonflexible materials, such as nonflexible plastic, the cassette parts and membranes may be cut into suitable lengths instead of being rolled onto the roller 570.

The production lines are equally applicable to the rotary embodiment of FIGS. 11 to 14. Instead of the cassette part proceeding down the production line in a linear fashion, they proceed around a circular production line in a rotary fashion.

Figure 18:
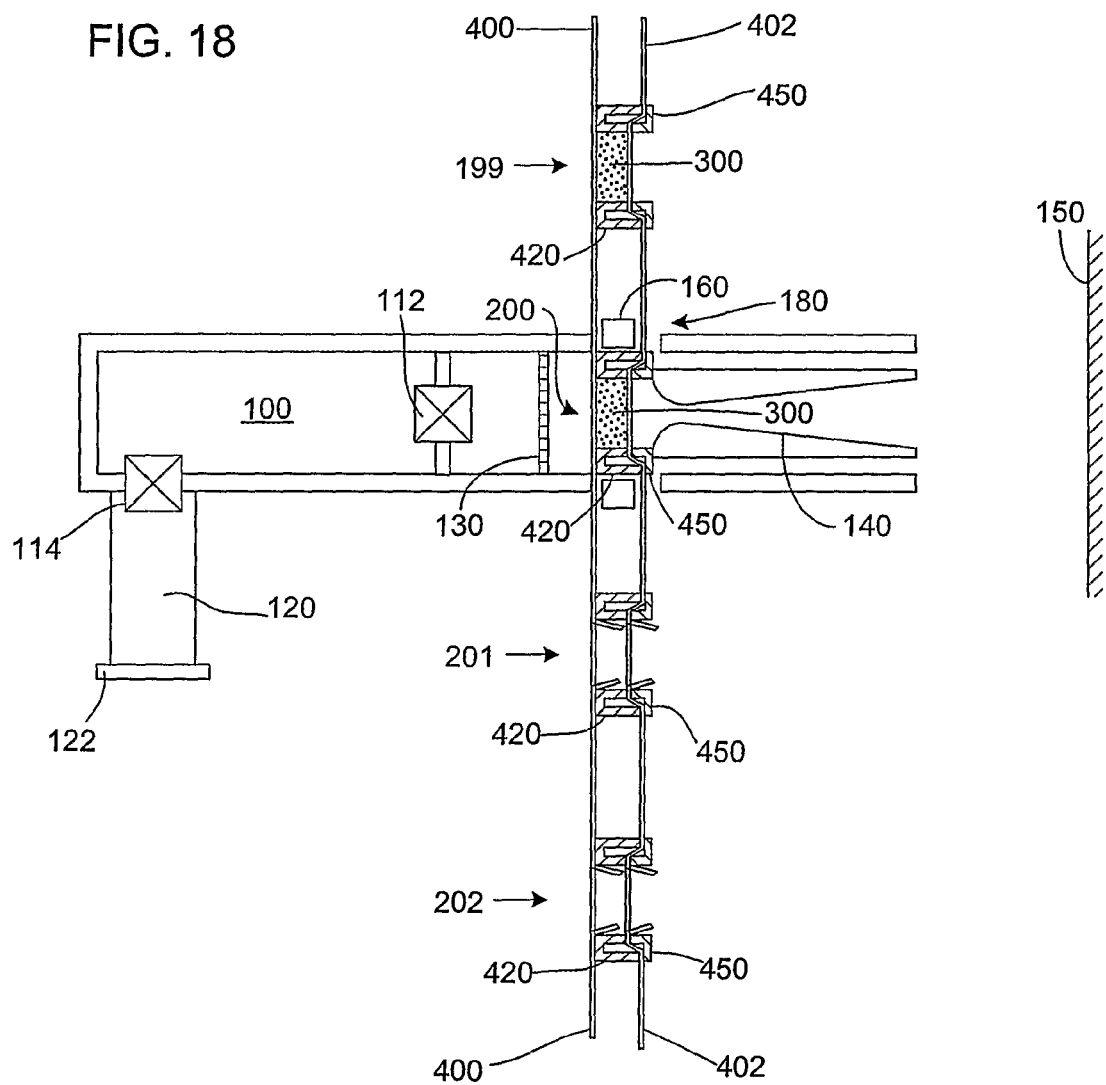
FIG. 18 shows a device according to the present invention adapted for multi-use.

FIG. 18 shows an embodiment of a device for accelerating particles according to the present invention. The nozzle 140 and filter 130 are substantially as illustrated in FIG. 1. In this embodiment, the self-contained reservoir of gas 100 is replaced by a volume 100 located between valves 112 and 114. The valve 112 is located downstream of the valve 114 and is preferably operatively connected to the actuation button of the device such that when the actuation button (not shown) is depressed, the valve 112 moves from a closed state to an open state.

The valve 114 is connected to a gas supply conduit 120 having a flange 122 or other suitable connection means to enable it to be connected to a large reservoir of pressurized gas. The valve 114 is selectively operable to allow pressurized gas to flow from the gas supply conduit 120 into the reservoir 100 where pressure is built up until the pressure in the reservoir 100 is equal to that of the pressurized gas source. Valve 114 is thereafter closed and the device may be disconnected from the pressurized gas source. Upon actuation, valve 112 opens and the pressurized gas in the volume 100 is exposed to the particle cassette 200 loaded in the device at that time.

FIG. 18 shows a strip of particle cassettes substantially as illustrated in FIG. 8, in which one of the cassettes 200 is lined up with both the exit of valve 112 and the entrance of nozzle 140. The device comprises a particle cassette exchange station 180 which is designed to receive, hold, release and expel particle cassettes. The particle cassette exchange station 180 comprises a holder 160 which in this embodiment comprises moveable arms that can grip the outside circumference of the particle cassette 200. Upon actuation, gas flows through the valve 112, from the volume 100, through the filter 130 and bursts the membranes 400, 402 of the particle cassette 200, thereby entraining the particles 300. The gas and entrained particles are then accelerated by the nozzle 140 and impact on the target 150.

Of course, it is perfectly possible to use the reservoir 100 and actuation button 110 shown in FIG. 1 as the means for supplying gas in the FIG. 18 embodiment. The use of valves 112 and 114 and gas supply conduit 120 is merely preferable for a multi-use device as this avoids the necessity of replacing the reservoir 100 (with its frangible tip 102) after each device activation.

After the device has been actuated and the particles 300 inside the particle cassette have been accelerated into the target 150, the holder 160 can be moved so as to release the spent particle cassette 200 and to capture and hold the next particle cassette 199 in line. FIG. 18 also shows spent cassettes 201, 202 in which the membranes 400, 402 have already burst.

Also not shown, it is convenient that the strip of particle cassettes is dispensed from a roll and that the strip of used particle cassettes is wound on another roll. The roll from which the particle cassettes are dispensed may be mounted on the device itself. Also, the roll onto which the used particle cassettes are wound may also be mounted on the device. This allows hundreds of injections to be carried out in succession without requiring the need for laborious cassette removal and replacement with a fresh cassette and without requiring laborious spent reservoir 100 removal and replacement with a fresh reservoir. The invention therefore has particular application to a multi-use device, such as might be desirable in mass immunization programmes.

Although FIG. 15 shows this principle being applied in the linear embodiment of FIG. 8, it can equally be applied to the circular embodiments by rotating the membranes 402 about the centre point 475.

Figure 19:
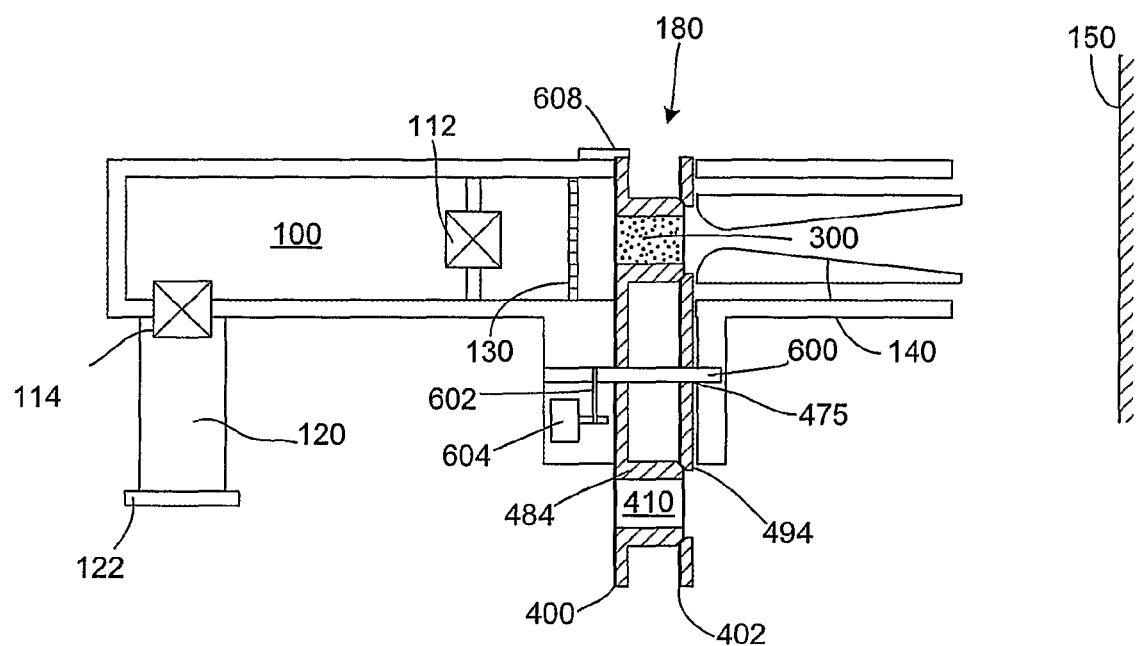
FIG. 19 shows another device according to the present invention adapted for multi-use.

FIG. 19 shows an embodiment of particle acceleration device which utilizes the unitary particle cassette of FIGS. 12, 13 and 14.

The device shown in FIG. 19 accepts a unitary particle cassette created by bringing together the first cassette part 484 of FIG. 12 with the second cassette part 494 of FIG. 13, in the manner shown in FIG. 14. A central hexagonal shaft 600 mounted in the device locates with the holes 475 in the first and second cassette parts. The shaft is connected by a belt 602 to a motor 604 in this embodiment such that the particle cassette can be rotated around its axis to bring different gas flow passages 410 into alignment with the nozzle 300. Any non-circular shape can be used for the shaft 600.

Figure 20:
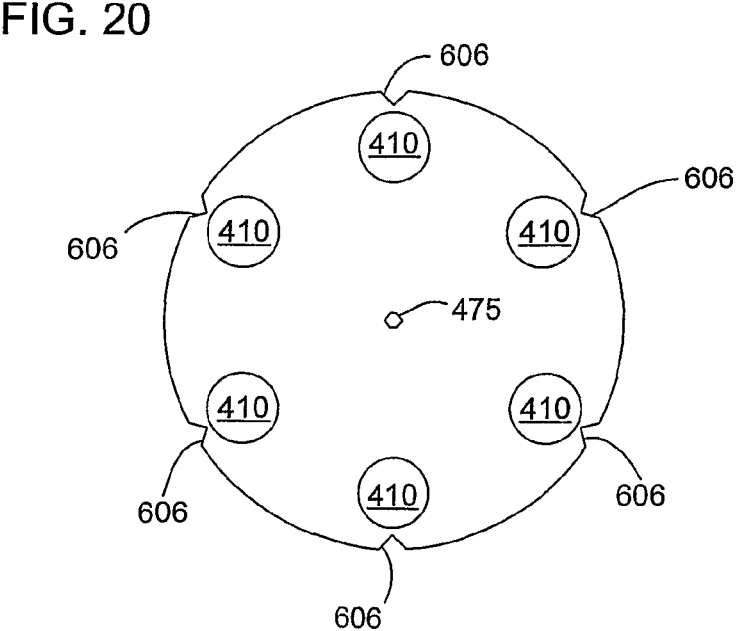
FIG. 20 shows a top view of a unitary circular particle cassette.

The first or second particle cassette parts may be provided with index notches 606, as shown in FIG. 20, which can be indexed by member 608 on the particle acceleration device. This allows the gas flow passages 410 to be properly aligned with the gas flow passages of the particle acceleration device. A non-circular index hole 475 is not required in this embodiment.

Of course, it goes without says that more gas flow passages 410 can be arranged in the particle cassette than the six shown in FIGS. 12 and 13.

We claim:

1. An article for use in manufacturing particle cassettes, the article comprising:
    a single piece of first membrane film capable of being ruptured by gas under pressure;
    a single piece of second membrane film capable of being ruptured by gas under pressure;
    a plurality of first cassette parts laterally offset from one another and attached to the first membrane film;
    a plurality of second cassette parts laterally offset from one another wherein each of the plurality of second cassette parts is attached to the second membrane film via a sealing face,
    wherein the plurality of first cassette parts are joined to the plurality of second cassette parts with the second membrane film interposed in between the plurality of first cassette parts and the plurality of second cassette parts, and
    wherein the plurality of first cassette parts and the plurality of second cassette parts form a gas flow passage.

2. The article of claim 1 wherein the plurality of first cassette parts are all arranged on the same side of the single piece of first membrane film.

3. The article of claim 1, wherein the plurality of first cassette parts are arranged on the single piece of first membrane film in a substantially linear formation.

4. The article of claim 1, wherein the plurality of first cassette parts are arranged on the single piece of first membrane film in a substantially circular formation.

5. The article of claim 1, wherein the single piece of first membrane film is attached to each of the plurality of first cassette parts by a heat bonding method.

6. The article of claim 1, wherein the gas flow passage has a dose of particles therein.

7. The article of claim 1, wherein the gas flow passage is closed by the first membrane film and the second membrane film to create a chamber for the confinement of particles between the first membrane film and the second membrane film.

8. The article of claim 1, wherein the plurality of second cassette parts are arranged on the same side of the second membrane film.

9. The article of claim 1, wherein the first and/or second membrane films rupture when a gas pressure differential of 15-60 bar exists thereacross.

10. A method of making an article for use in manufacturing particle cassettes, the method comprising:
    passing a single piece of first membrane film through a roller; and
    attaching a plurality of first cassette parts to the single piece of first membrane film by bringing together a first platen carrying the plurality of first cassette parts and a second platen,
    wherein the plurality of first cassette parts are laterally offset from one another, and wherein each of the plurality of first cassette parts defines a gas flow passage closed off at one end by the single piece of first membrane film.

11. The method of claim 10, wherein the plurality of first cassette parts are arranged on the same side of the single piece of first membrane film.

12. The method of claim 10, further comprising, after the attaching step providing a dose of particles that is retained in each respective gas flow passage.

13. The method of claim 12, further comprising:
closing the gas flow passage with a second membrane film so that the dose of particles is confined to a chamber between the first membrane film and the second membrane film, and wherein the second membrane film is a single piece of film closing each of the plurality of gas flow passages, and further comprising rolling up the first and/or second membrane film to provide a roll of particle cassettes, and further comprising scoring the first and/or second membrane film to allow easy detachment of one or more particle cassettes from the first and/or second membrane film, and further comprising cutting the first membrane film around the perimeter of each gas flow passage.

14. The method of claim 12, further comprising:
conveying the first membrane film with the plurality of first cassette parts retaining the dose of particles to a cassette assembling station;

pressing a plurality of second cassette parts onto the plurality of first cassette parts at the cassette assembling station, wherein the plurality of second cassette parts is attached to a single piece of second membrane film, and wherein each of the plurality of second cassette parts defines an additional part of the gas flow passage and the gas flow passage is closed off at another end by the single piece of second membrane film.

15. The article of claim 1 wherein the sealing face of each of the plurality of second cassette parts is an annular surface configured to deform when in contact with another sealing face of the first cassette part and wherein the sealing face of the first cassette part is tapered.

16. The article of claim 1 wherein each of the plurality of second cassette parts has a filleted edge at a section of each of the plurality of second cassette parts that attaches to the second membrane film.

17. The method of claim 10, further comprising heating the second platen to head bond the plurality of first cassette parts to the single piece of first membrane film.

18. The method of claim 10, further comprising sterilizing the plurality of first cassette parts.

* * * * *